United States Patent [19]

Owen

[11] 4,175,422
[45] Nov. 27, 1979

[54] GAS MONITORS

[75] Inventor: Leslie J. Owen, Porthcawl, Wales

[73] Assignee: British Steel Corporation, London, England

[21] Appl. No.: 826,649

[22] Filed: Aug. 22, 1977

[30] Foreign Application Priority Data

Aug. 27, 1976 [GB] United Kingdom ............... 35790/76

[51] Int. Cl.² .......................................... G01N 27/04
[52] U.S. Cl. ..................................................... 73/23
[58] Field of Search ......................... 73/23, 27 R, 29; 338/34

[56] References Cited

U.S. PATENT DOCUMENTS

| | | | |
|---|---|---|---|
| 2,638,783 | 5/1953 | Rittner et al. | 73/29 |
| 2,687,342 | 8/1954 | Strange et al. | 73/27 R |
| 3,039,053 | 6/1962 | Jacobson | 73/29 |
| 3,567,387 | 3/1971 | Jones | 73/29 |
| 3,578,409 | 5/1971 | Silverman et al. | 73/27 R |
| 3,864,628 | 2/1975 | Klass et al. | 73/23 |
| 3,952,567 | 4/1976 | Shinagawa et al. | 73/23 |

*Primary Examiner*—Stephen A. Kreitman
*Attorney, Agent, or Firm*—Bacon & Thomas

[57] ABSTRACT

A gas sensor having a sensitive element of semi conductor type, the sensor being contained within an enclosure adapted to permit gas to come into contact with the element and incorporating means for maintaining adjacent the element, a substantially constant relative humidity.

13 Claims, 3 Drawing Figures

GAS MONITORS

This invention relates to gas monitors, and is particularly, although not exclusively, concerned with monitors capable of detecting the existence of toxic gases such as carbon monoxide in an air ambient.

The present invention is concerned with monitors in which the gas sensor comprises an electrically heated semi-conductor element whose resistance varies as a function of adsorbed gas. Typically such elements contain a suitably doped metal oxide and examples of this type of sensor are disclosed in U.K. Pat. No. 1374575.

Sensors of the type with which the present invention is concerned generally are incorporated into one arm of a bridge or other resistance-sensitive underwork so that changes in resistance brought about by variation in the concentration of a constituent in the ambient surrounding the sensor can be detected and registered. The relative sensitivity of the sensor to different constituents can be modified by selecting the operating temperature of the semi-conductor element and a temperature for detecting specific gases is achieved by adjusting the level of the sensor heating current.

It has been found that notwithstanding a high degree of heater current and temperature control, the sensitivity of a sensor of the type in issue varies in time to an extent which significantly affects the reliability of a gas monitor in which the sensor is embodied. An example of such variation is shown in FIG. 1 of the accompanying drawings which illustrate the sensitivity variation to carbon monoxide of a Figaro Type 712 and 812 Monitor over a 24-hour period selected at random. This variation is typical of other periods.

The present invention is based on the discovery that the sensitivity of sensor elements of the semi-conductor type is dependent upon the concentration of water vapour in the ambient under test.

According to one aspect of the present invention, a gas sensor incorporating a sensor element of the semi-conductor type is contained within an enclosure adapted to permit gas to come into contact with the element and incorporating means for maintaining adjacent the element a substantially constant relative humidity.

The relative humidity may be maintained at a constant level by desiccating the ambient adjacent the sensor element, by way of the means well known in the art.

In a preferred embodiment of the invention, the relative humidity is maintained at substantially 100% level conveniently by passing the gas under test through a pad which is gas-permeable and which is saturated with water. The pad, which may be of felt, foam, or the like, conveniently is maintained in a substantially saturated condition by direct or indirect contact with a water reservoir. Indirect contact may be maintained by an extended wick having one end in contact with the pad and having its other end immersed in the reservoir.

Alternatively, the water saturated pad may be disposed immediately adjacent the sensor element, and the gas may be permitted to come into contact with the element by diffusion through the pad.

An embodiment of the invention will now be described by way of example with reference to the accompanying drawing in which FIG. 1 is a curve showing the variation of sensitivity with time of a conventionally mounted sensor.

FIG. 3 is a curve showing the variation of sensitivity with time of a sensor mounted in accordance with the present invention.

Figure 2:
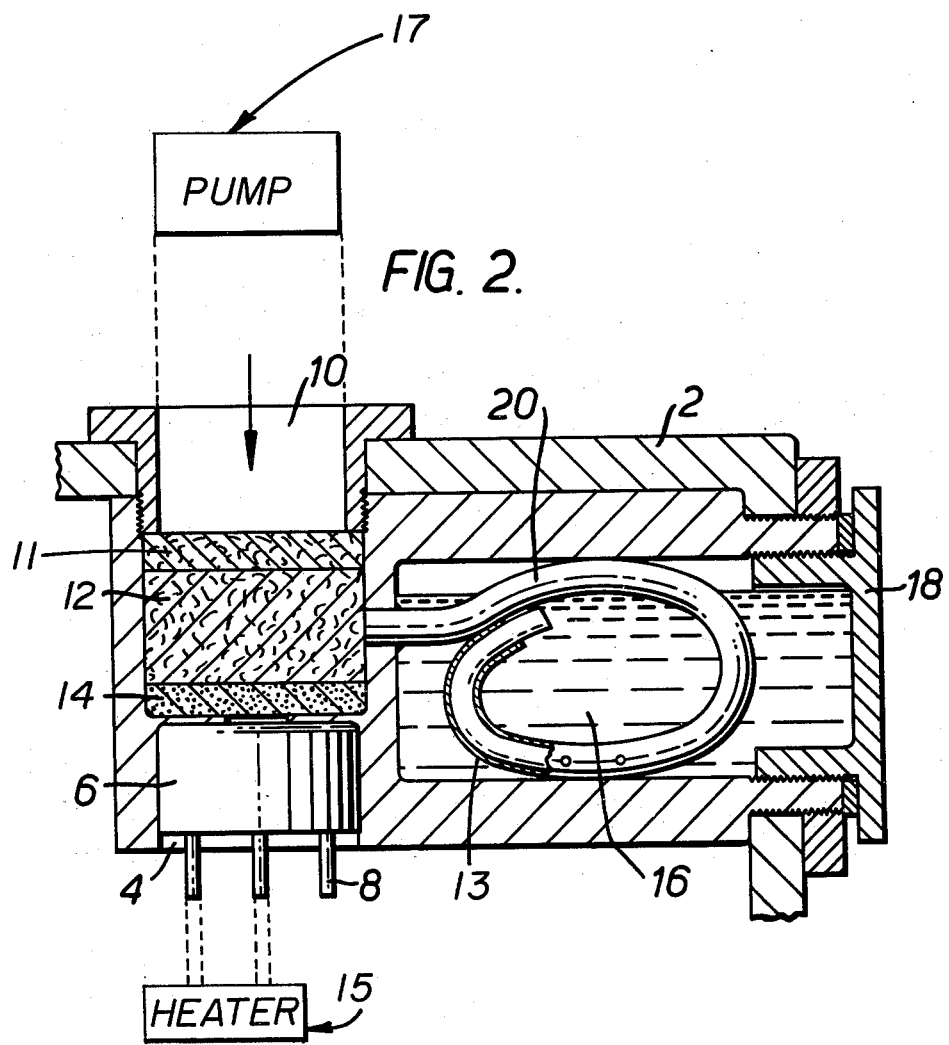
FIG. 2 is a sectional side view of a housing according to the present invention for a sensor of the semi-conductor type.

Referring to FIG. 2, the housing comprises an outer wall 2 of PVC or other inert material containing a plurality of recesses which may be formed by machining or during casting. One recess, indicated generally at 4, houses the sensor 6 which may be of the semi-conductor type embodied in inter alia the Figaro Monitor Type 712 and 812. Recess 4 is of sufficient depth to firmly retain the sensor in position while permitting the external pins connected to the sensor element and to the electrical heater 15 to be plugged directly into the monitor circuit.

The inner face of the recess 4 is provided with an opening through which the sensor element can come into contact with the ambient gas and with the vapour from a water source effective to stabilise sensitivity. The sensor housing forms an interference fit with the walls of the recess, to prevent ingress of gas from other than the opening.

The gas ambient is applied to the sensor through an inlet 10 which communicates with the recess 4 by way of a dust filter 11, a humidifier pad 12 and a semipermeable membrane 14, for example of Vyon (Registered Trade Mark) produced by Industrial Division of Povair. A pump 17 may be provided to enable gas to be pumped through pad 12 into contact with the sensor element.

The gas ambient comes into contact with the sensor 6 by diffusion through the combination of the filter humidifier and membrane, and all these elements are selected to permit such diffusion to occur.

The gas brought into contact with the sensor 6 is humidified in this embodiment to substantially 100 percent relative humidity by passing through the pad 12 which is maintained saturated with water derived from a reservoir defined by a further sealed recess 16 in the sensor housing. The reservoir is sealed by a water-tight filler cap 18 and delivers water to the humidifying pad 12 by way of a wick 20 of foam, felt or like material. The wick is provided with a PVC or other inert and water-impermeable sheath 13 along all but its end regions to ensure some degree of control over the rate at which water is delivered from the reservoir to the humidifier, and to ensure that the pad remains permeable to gas diffusion.

Figure 1:
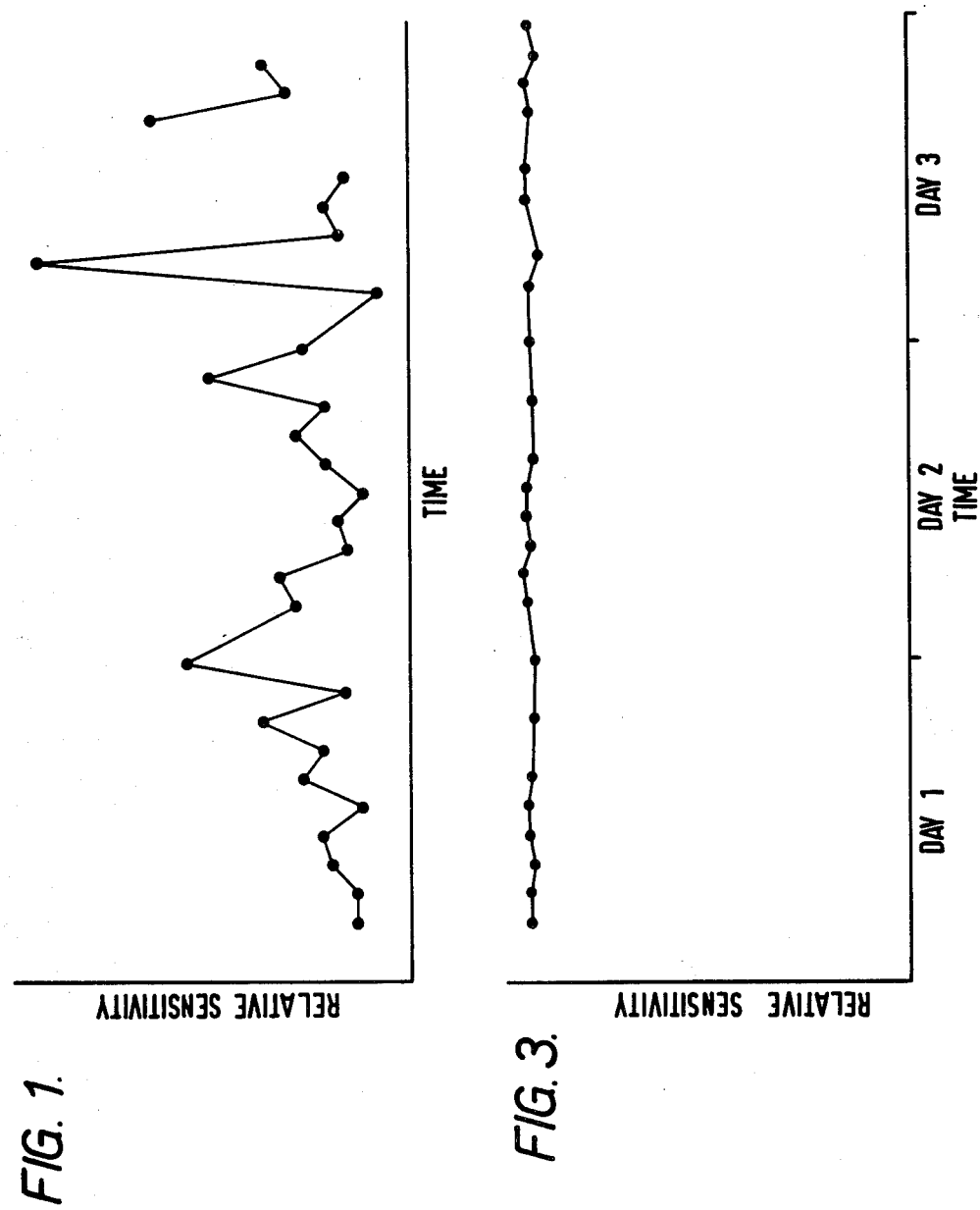

Gas incident upon the sensor element and substantially saturated with water vapour has the effect of stabilising the sensitivity of the sensor to the selected contaminant in the gas under test. As hereinbefore described, the relative sensitivity to the contaminant is achieved by control of the sensor element temperature, and different temperatures have been found not to affect the improvement in stability achieved by the invention. FIG. 3 shows the variation in sensitivity achieved by the arrangement of the invention; a comparison with the variation of sensitivity indicated in FIG. 1 illustrates the level of improvement achieved.

The water level in the reservoir 16 may be checked by providing a suitable window, conveniently in the filler cap 18. Alternatively, exhaustion of the water supply may be detected by measuring the electrical conductivity of the pad 14 for example by way of electrodes inserted in the pad.

We claim:

1. A gas sensor, having a sensitive element of semiconductor type, the sensor being contained within an enclosure adapted to permit gas to come into contact with the element, wherein the enclosure incorporates a humidifier which maintains adjacent the element, a substantially constant relative humidity, and wherein said humidifier comprises a water absorbant pad disposed adjacent the sensor element, and arranged to communicate with a water reservoir.

2. A gas sensor as claimed in claim 1 wherein an electric heater is disposed to vary the temperature of the element, to modify its relative sensitivity to different gases.

3. A sensor as claimed in claim 1 wherein the water absorbant pad is gas permeable when saturated and is disposed between the sensor element and the gas ambient under test.

4. A sensor as claimed in claim 3 wherein the enclosure is adapted to enable gas to be pumped through the pad into contact with the sensor element.

5. A sensor as claimed in claim 3 wherein the enclosure is adapted to enable gas to reach the sensor element by diffusion.

6. A sensor as claimed in claim 1 wherein the pad communicates with the water reservoir by way of a wick.

7. A sensor as claimed in claim 6 wherein the wick is provided with a water impermeable sheath along a length intermediate the end regions.

8. A gas monitor incorporating a sensor as claimed in claim 1.

9. A gas sensor as claimed in claim 1, wherein the pad maintains a relative humidity at substantially 100%.

10. A gas sensor as claimed in claim 1, wherein the pad is arranged to communicate directly with the water reservoir.

11. A gas sensor as claimed in claim 1, wherein the pad is arranged to communicate indirectly with the water reservoir.

12. A gas sensor having a sensitive element of semiconductor type, the sensor being contained within an enclosure adapted to permit gas to come into contact with the element, a water reservoir being arranged to communicate with the enclosure so as to maintain adjacent the element a substantially constant relative humidity.

13. A gas sensor having a sensitive element of semiconductor type, the sensor being contained within an enclosure adapted to permit gas to come into contact with the element, and incorporating means for maintaining adjacent the element, a substantially constant relative humidity wherein said means is a humidifier effective to introduce moisture to the region adjacent the sensor element.

* * * * *